United States Patent [19]

Brekke

[11] 4,186,448
[45] Feb. 5, 1980

[54] DEVICE AND METHOD FOR TREATING AND HEALING A NEWLY CREATED BONE VOID

[76] Inventor: John H. Brekke, 4921 Pike La., Rte. #1, Duluth, Minn. 55811

[21] Appl. No.: 853,417

[22] Filed: Nov. 21, 1977

Related U.S. Application Data

[63] Continuation-in-part of Ser. No. 677,752, Apr. 16, 1976, abandoned.

[51] Int. Cl.² .................. A61F 1/24; A61B 17/18
[52] U.S. Cl. .................. 3/1.9; 128/92 B; 128/92 G; 128/334 R; 128/296; 3/1
[58] Field of Search .................. 3/1, 1.9; 128/92 R, 128/92 B, 92 BC, 92 G, 334 R, 335.5, 325, 296

[56] References Cited

U.S. PATENT DOCUMENTS

| 2,465,357 | 3/1949 | Correll | 128/296 X |
|---|---|---|---|
| 2,610,625 | 9/1952 | Sifferd et al. | 128/296 |
| 2,621,145 | 12/1952 | Sano | 128/92 G |
| 3,491,760 | 1/1970 | Braun et al. | 128/335.5 |
| 3,636,956 | 1/1972 | Schneider | 128/335.5 |
| 3,688,317 | 9/1972 | Kurtz | 128/334 R |
| 3,739,773 | 6/1973 | Schmitt et al. | 128/92 BC |
| 3,902,497 | 9/1975 | Casey | 128/296 |
| 3,937,223 | 2/1976 | Roth | 128/296 |

Primary Examiner—Ronald L. Frinks
Attorney, Agent, or Firm—Wicks & Nemer

[57] ABSTRACT

Device and method for treating a newly created bone void or soft tissue deficiency including a one piece moldable body having a form sufficient to cover a bone void and made of a biodegradable material. The body includes enclosed interconnected randomly positioned, randomly shaped and randomly sized voids extending throughout the mass of the body member with each void communicating with the others and communicating with substantially the entire exterior of the body to which blood is attracted by capillary action from arteries leading to the bone void for saturation of the body with blood for the development of blood capillaries whereby the bone void is healed as the body member biodegrades.

8 Claims, 17 Drawing Figures

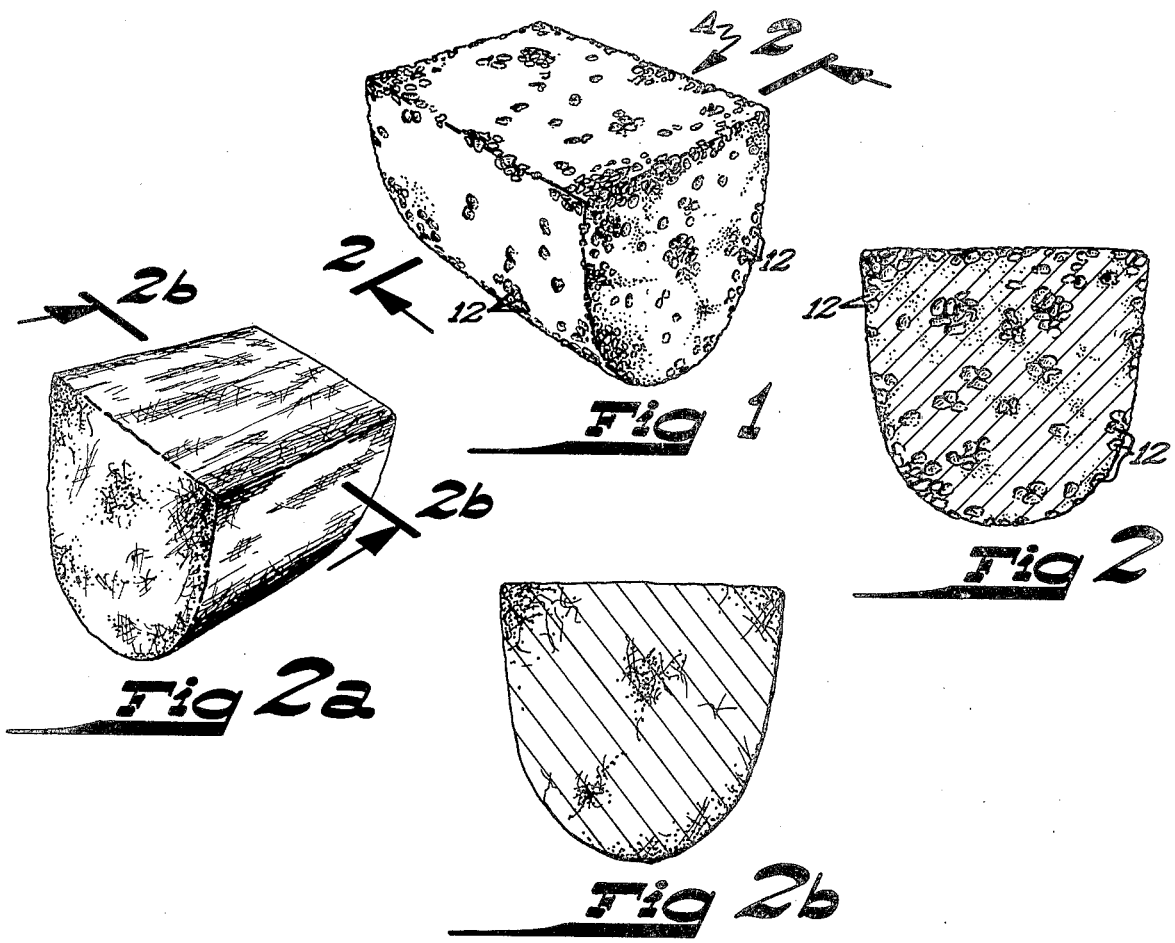
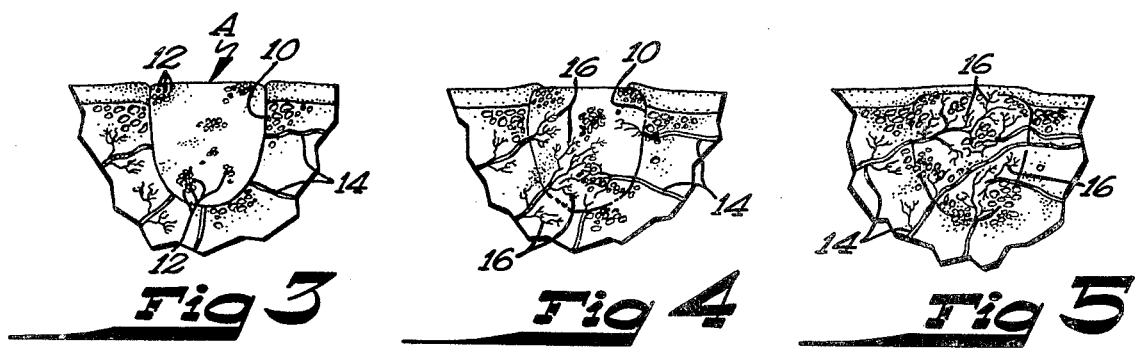
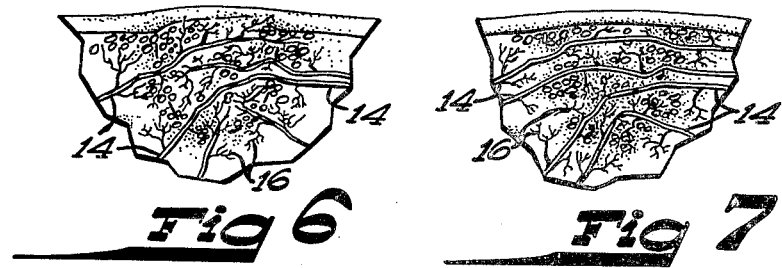

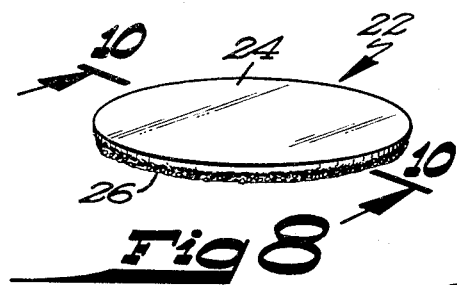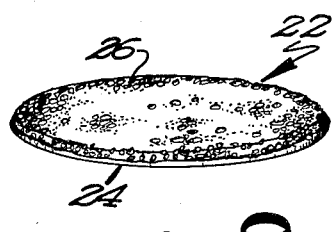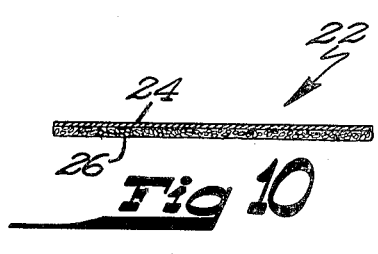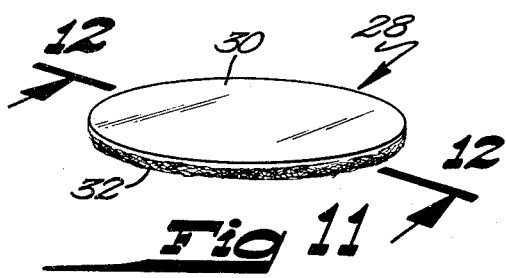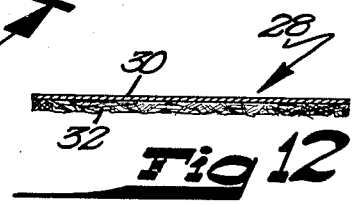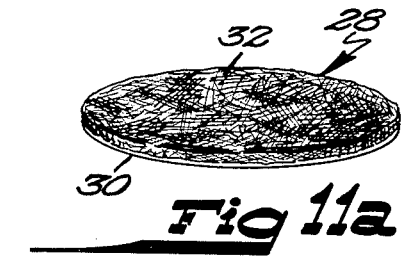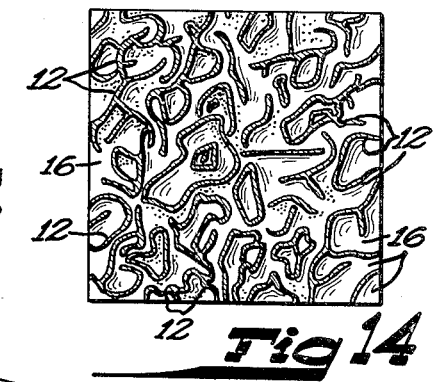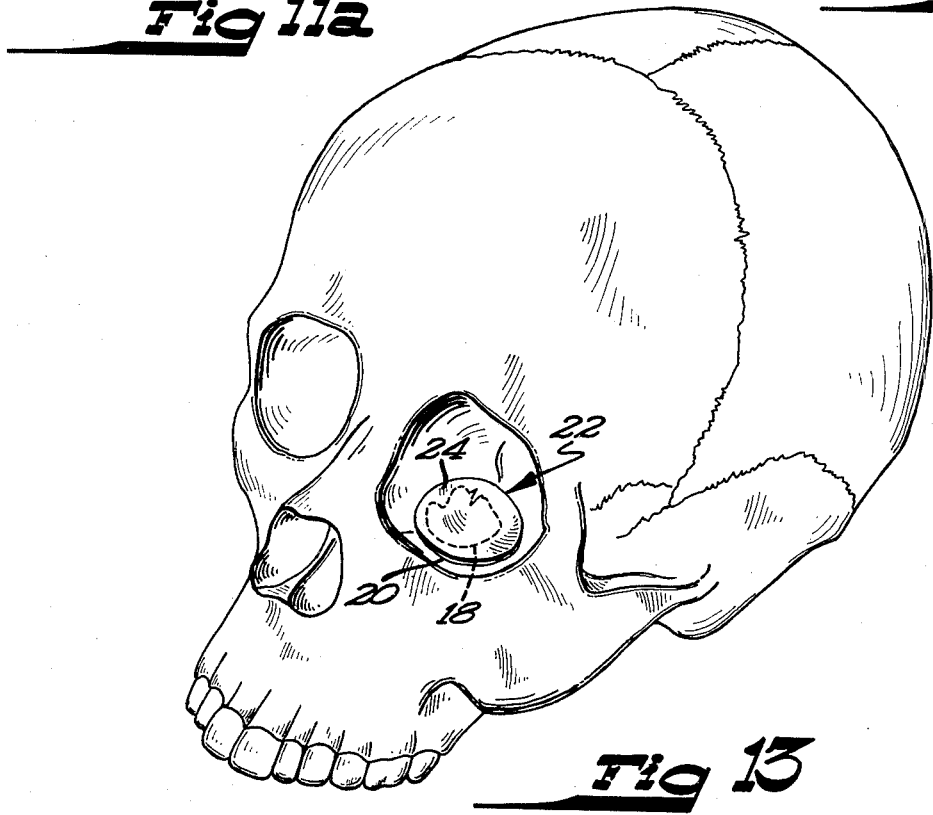

DEVICE AND METHOD FOR TREATING AND HEALING A NEWLY CREATED BONE VOID

This application is a continuation-in-part of applicant's application Ser. No. 677,752, filed Apr. 16, 1976, and now abandoned.

SUMMARY

The invention relates to a device and method of treating newly created bone voids, e.g. that produced by a tooth extraction, removal of bone pathology or where there is a significant loss of skelatal structure such as in the fracture—displacement of the bones, as one example, the bones supporting the contents of the eye cavity.

It is an object of the invention to provide a one piece molded body member for filling or covering a bone void or soft tissue deficiency which body member attracts blood in fluid suspension by capillary action until clotting forms which ultimately leads to the formation of tissue and/or bone. The member is a one piece porous body with enclosed randomly sized, randomly positioned and randomly shaped interconnecting voids, each void communicating with all the others, and communicating with substantially the entire exterior of the body and through which blood is attracted by capillary action throughout all of the voids of the body member. With this unique construction allowing all the voids to connect with all other voids there is no resistance from the body filaments forming the voids to the development of new capillaries. With all the voids communicating with the exterior of the body member the body can receive the supply of blood from the arteries bordering the bone or tissue void in numerous places at the exterior of the body member.

With each void connected with every other void, blood capillaries grow from the exterior of the body member supplied by arteries at the sides of the bone void or tissue void to the center and throughout the body member, for there are no blocking or dam-like layers or members in the instant body member to prevent capillaries from forming throughout the body member due to the construction of the body meshwork. The voids comprise about 90% of the mass of the body member.

A multiplicity of points on the surface of the body member have an avenue of access through the interconnected voids to the center of the body member and to all other voids wherein capillaries are therefore capable of being formed. Thus, capillaries form at random throughout the body member because the random structure of the body filaments forming the voids eliminates resistance to new capillary development throughout the body, thus encouraging to a high degree new blood vessel formation. The voids may be formed by a vacuum foaming process or by a process of forming connected spun filaments. The voids fill with blood due to capillary action such action being assisted by incorporation into the body of a wetting agent such as Ultrawet 60L(T.M.) sold by the Fisher Scientific Company of Chicago, Ill., with sodium oleate being a further example of a wetting agent. The result is the forming of interconnected strands of clotted blood throughout the body member.

The body member is made of biodegradable material such as polylactic acid as an example of biodegradable polymers synthesized from members of the organic chemistry group of compounds known as hydroxy acids. It has been found that the polylactic acid body maintains its structural integrity as the body member is inserted into the bone or tissue void the interconnection of voids throughout the body member is not diminished even if the body is subjected to compressive forces. Compression together of body structural elements in known body elements form dams or physical barriers which prohibit the free flow of fluid blood throughout the entire body member and therefore prevent the formation of capillaries throughout the body member.

When that situation exists using known body elements (absorbable or biodegradable material) a dead space will ultimately be created after the material has been absorbed or degraded. In the bone environment this sequence of events produces a bone cyst, whereas in the soft tissue environment a similar cystic cavity is produced. Such cysts can increase in volume, harbor contaminated debris and bacteria and can ultimately reach pathologic proportions.

Additionally, the body member, as disclosed herein, maintains its structural integrity long enough to assure optimum development of new blood vessels and granulation tissue throughout the entire volume of the body member. When the member becomes saturated with blood, the blood clots, but the clot differs from a common blood clot in that the meshwork blood clot formed in the voids is held in suspension within the voids throughout the member rather than as a solid mass of coagulated blood. With the interconnected randomly positioned voids in the body, which also communicate with the exterior of the body, the strands of clotted blood pursue a full and normal maturation process. By the time the blood clot formed in the meshwork reaches full maturation into scar tissue and/or bone, the body filaments are completely biodegraded. Further, with the body member in the void the amount of blood required to fill the void and clot is less than without the subject method and device.

It has been found that the human body cannot distinguish between its own hydroxy acids and the polylactic acid material of the body member so there is no rejection of or adverse biologic response to the body member. The construction of the body member allows fibroblasts to grow on the polylactic acid filaments of the body member and new capillaries to grow through the voids and upon the filaments of the member. Fibroblasts synthesize scar in the process known as "fibroplasia". Fibroblasts migrate into the body member along the fibrin strands produced as the end result of the clotting process. Fibroblasts also migrate into and throughout the voids of the body member and along the polylactic filaments while capillaries grow by endothelial budding into the voids of the body member all accomplished by means of the construction of the body member herein disclosed. The fibrin strands and the fibroblasts can extend throughout the body member due to the random voids connecting with all other voids in the body member.

In some instances the patient is afflicted with a coagulation defect, and it is an object of the invention to impregnate the polylactic acid filaments of the body member with a hemostatic agent such as thrombin or thromboplastin so that the structural filaments holds the therapeutic material and not the voids, thereby leaving the voids unchanged so that capillaries may be formed within the voids as described above and the process of granulation tissue maturation may continue as usual in spite of the presence of a therapeutic agent in the structural filaments. With the material so impregnated it assists coagulation in two ways, (1) by the member functioning as a mechanical matrix for the coagulation process as well as reducing the volume of blood needed to occlude the surgical void and (2) the hemostatic agent, being gradually released from the biodegradable material, chemically interacts with the patient's own functional coagulation factors in such a way as to reduce the effects of the patient's coagulation factor deficit. The polylactic acid structural filaments may also be impregnated with a variety of therapeutic agents to protect and improve the healing process of the tissues involved. While the Schmitt U.S. Pat. No. 3,739,773 discloses a bone void dressing of a biodegradable material (polyglycolic acid) it does not suggest the structure of the instant body member made of polylactic acid which has unobstructed voids each connected with all the other voids. Without the body member structure herein disclosed the healing process of the body cannot take place.

The body member differs from the prior art in (a) form, (b) chemical composition, (c) mechanism of action and (d) the capability of the body member. None of the prior art suggests the combination of (a), (b), (c) and (d) aforementioned.

The invention will appear more clearly from the following detailed description when taken in connection with the accompanying drawings, showing by way of examples preferred embodiments of the inventive idea wherein like numerals refer to like parts throughout.

In the drawings forming part of this application:

FIG. 1 is a perspective view of a bone void dressing member embodying the invention.

FIG. 2 is a sectional view of the line 2—2 of FIG. 1.

FIG. 2a is a further embodiment of a bone void dressing member.

FIG. 2b is a sectional view on the line 2b—2b of FIG. 2a.

FIG. 3 is a sectional view of the dressing shown in FIG. 1 as an example in a bone void produced by a dental extraction two-thirds saturated with blood.

FIG. 4 is a view similar to FIG. 3 but with the dressing completely saturated with blood.

FIG. 5 is a view similar to FIG. 4 but with the condition substantially four months old wherein there is solid tissue formed replacing clotted blood shown in FIGS. 3 and 4, and the thickness of all the dressing member partitions reduced about 75% by metabolism (biodegregation).

FIG. 6 is a view similar to FIG. 5 but with a condition substantially six months old wherein the tissue areas are coalesced and with only islands of the dressing member remaining.

FIG. 7 is a view similar to FIG. 6 but with the dressing totally metabolized and the cavity healed.

FIG. 8 is a perspective view of an orbital floor implant made in accordance with the invention.

FIG. 9 is a perspective view similar to FIG. 8 but of the opposite surface.

FIG. 10 is a sectional view on the line 10—10 of FIG. 8.

FIG. 11 is a perspective view of a further embodiment of the implant of FIGS. 8, 9 and 10.

FIG. 11a is a view similar to FIG. 11 but with the embodiment reversed top and bottom.

FIG. 12 is a sectional view on the line 12—12 of FIG. 11.

FIG. 13 is a perspective view of a portion of a human skull in the area of the eye orbit and sinus showing the orbital implant in position over a void in the orbital floor, the void shown in broken lines.

FIG. 14 is a representative enlarged section through a portion of the bone void dressing member of FIGS. 1-14.

Referring to the drawings in detail, the bone void dressing in one form is cellular in the form of a plug or body member such as A, particularly FIGS. 1 and 2. The porous meshwork plug A is formed of a polyhydroxy acid such as polylactic acid herebefore referred to with voids including interconnected and randomly sized, randomly positioned, and randomly shaped voids, 12 extending throughout the body, each void connecting with every other void and leading to the exterior surface of the plug. The high molecular weight of the polyhydroxy polymer is converted into the interconnecting cellular voids by processes such as high vacuum foaming well known in the plastics industry. Further, the polyhydroxy acid is biodegradable.

Generally speaking the upper jaw bone has a supply of blood which promotes adequate healing of a bone void resulting from, for example, the extraction of a tooth. A blood clot in a bone void requires an intrabony supply of blood in order to be converted into tissue and bone. It is generally agreed that the supply of blood to the lower jaw is not as plentiful as that to the upper jaw, and it is frequently inadequate to nourish newly formed blood clots in newly formed bone voids. It has been found that about ten to twenty percent of persons having tooth extraction in the lower jaw, third molar area, have a deficient supply of blood and as a result develop what is known as a "dry socket" with the attendant problem of pain in the socket prior to complete healing and extended time for buildup of tissue and bone with complete healing. With the present invention, the "dry socket" complication is eliminated, immediate post operative hemorrhage is greatly reduced and the processes of granulation tissue maturation and final rebuilding of tissue appropriate for the particular environment of the wound are all improved in speed and efficiency.

Again with reference to the figures in the drawings, in FIG. 1, the polyhydroxy acid is formed as a porous plug body A adapted to be inserted, in one example, in the bone void 10 formed by the extraction of a tooth. The molded one piece porous body A includes a multiplicity of randomly sized, randomly shaped and randomly positioned interconnected voids or interstices 12, which form a multiplicity of interconnections, see FIG. 14 in particular. Each void connects with every other void and with the outer surface of the plug. After the bone void is created, as for example by the extraction of a tooth, the body member A having a wetting agent incorporated therewith is then positioned in the void where it functions to attract fluid blood throughout its entire substance by capillary action through the interconnected interstices or voids of the body material, such action being assisted by incorporation of a wetting agent hereinbefore referred to into the body material.

With the plug in the bone void and saturated with blood, it applies pressure to the intrabony sources of active bleeding by occupying fully the bone void. The sources of bleeding are the arteries which lead through the bone to the voids at the outer surfaces of the plug body and the pressure aids in stopping bleeding while simultaneously providing the necessary mechanical attachment of the blood saturated body member to a continuous source of blood supply which are the arteries illustrated as 14 at the sides of the void 10 as illustrated in FIG. 3. The arteries bring blood to the body A and with the voids leading inwardly from all sides of the plug in random fashion and connecting each with the other, capillaries form freely and easily throughout the plug thereby providing the necessary sources of nutrition to the developing of granulation tissue as well as a source for conducting fibroblasts to all portions and areas of the bone or tissue void. This enhances the rate and efficiency of the tissue healing process to a degree hitherto impossible.

As soon as the body A becomes saturated with fresh blood, the blood within the interstices of the plug begins the coagulation process and forms a normal blood clot. However, the blood clot in the member differs from a common blood clot in that the blood clot in the member is held in suspension within and by the framework of randomly interconnected voids of the body in the form of numerous individual strands of clotted blood throughout the plug member. These strands are formed by blood travelling from the arteries at the sides of the bone void into the voids of the body A. The body A has the ability to hold a clot composed of numerous strands 16 of clotted blood in suspension within and throughout the voids of the entire framework of the plug, see FIG. 3. The polylactic body with the random interconnected voids maintains its structural integrity, that is, as the body A is forced into the bone void, the compression of the same does not close off the connected voids. This maintenance of the structural integrity is maintained long enough to assure optimum development of new capillaries, maturation of granulation tissues, and final appropriate i.e. bone or soft tissue before it biodegrades.

Each individual strand of clotted blood proceeds to mature as would any common blood clot. As the blood strands mature, the same metabolize the supporting filaments of polylactic acid between which the voids are formed. Each strand of maturing blood clot increases in strength and volume at the expense of the supporting polylactic acid filaments. The result of this process is that by the time the blood clot has reached full maturation into scar tissue and/or bone, the body member has been completely metabolized by the cells of the member body blood clot, granulation tissue and final mature tissue. When the wound has healed the body member has ceased to exist.

With the plug body A herein referred to and what it does, the amount of blood clot in the bone or tissue void that required nourishment is lessened. Blood nourishment is from the intrabony arteries at the sides of the bone void and the plus attracts fluid blood from the arteries. With less blood supplied to the lower jaw, as explained above, and with less required with the plug, chances of healing uneventfully are improved. In addition, the polylactic body member clot, by virtue of the body's holding a smaller volume of blood clot in the form of numerous clot strands in suspension, eliminates the logistical problems associated with supplying blood from a limited number of intrabony arterial souces to a common homogeneous large volume clot which has a limited outer surface area.

The interrelated strands extending throughout the voids will allow for easier formation of new capillaries extending from the arterial sources directly into the center of the clot of the body member thereby supplying blood more evenly throughout the entire volume of the body member clot rather than relying on the slow development of new capillaries from the limited surface area of a relatively large volume homogenous blood clot where the body member is not used.

Bone voids are produced by several different developmental and pathologic conditions. Although bone voids can occur in any member of the skeletal structure, they occur most frequently in the maxilla (upper jaw) and mandible (lower jaw). This discussion, therefore, is directed toward the use of the polylactic acid material of both FIGS. 1 and 2a, the material of FIG. 1 being a closed but ubiquitously interconnected cell body member and the material of FIG. 2a being spun filaments having interconnected randomly positioned, randomly sized and randomly shaped voids to promote uneventful healing of bone voids in the maxilla and mandible.

Bone voids are produced in the maxilla and mandible whenever a tooth is extracted. Bone voids of larger proportions are produced whenever a pathologic lesion such as a cyst or central bone tumor are removed. The polylactic acid member can be used to great advantage as described previously in promoting rapid, uneventful healing of these larger bone voids as well as those produced by dental extraction.

A particularly vexing problem sometimes occurs when the extraction of a maxillary posterior tooth results in direct communication with the upper jaw sinus. This condition can lead to development of an oral/antral fistula which occasionally requires an additional surgical procedure to close. The polylactic acid body member is usable to great advantage in this instance also to promote rapid and uneventful healing of the extraction would thereby occluding the oral/antral communication.

A common problem resulting from severe maxillofacial trauma is a significant loss in integrity of skeletal structure (orbital floor) which supports the contents of the eye orbit. Loss of a sufficient area of orbital floor results in a herniation of orbital contents (fat and muscle) located just below the orbital floor. The consequences of such a herniation of orbital contents into the upper jaw sinus into the sinus are lowered pupillary level of the affected eye and possible entrapment of extraoccular musculature between fractured bone fragments. Both of such consequences can, if not corrected, produce significant diplopia (double vision) due to the lowering of the eye and loss of extraoccular muscle function.

A number of materials in the form of flat members are currently being used as orbital floor prothesis to artificially support orbital contents in normal position, free of healing bone fragments. Two of the most common of these flat members are made from the materials TEFLON (TM) and supramid (TM). The two last mentioned materials are prepared of inert substances and formed into very thin sheets which are surgically inserted across the opening or fracture in the orbital floor between intact orbital floor bone and the orbital soft tissue contents. Although members made of these materials have provided success in the treatment of severe orbital floor fractures, the same carry the significant disadvantage of remaining intact and permanently in place. On occasion, therefore, the members can become dislodged from their original positions which produces occular irritations, impairment of occular mobility and occasional sequestration through the incision used to insert the members. A sheet of polylactic acid as herein described is made of a thinness to be acceptable as an orbital floor implant member and as such it provides equal stability for orbital contents but is gradually metabolized as the clotted blood which it supports is converted into the bone and scar tissue. The highly desirable advantage of polylactic acid as hereinafter described material as an orbital floor implant is that it provides a floor or support for the orbital contents and then ceases to exist being biodegradable after the orbital floor has healed.

Referring to FIG. 13 there is illustrated the void 18 in the orbital floor 20. Positioned on the floor is the one piece implant 22 of FIGS. 8, 9 and 10, which is made of polylactic acid with the upper or first solid smooth continuous surface layer 24 of a thickness of about 0.5 mm of polylactic acid with the integral second or lower layer 26 of polylactic acid in the form of interconnected randomly positioned, randomly shaped and sized voids, each void connected with the others and extending to the outer surface of the layer 26 as hereinbefore described with reference to body member A. The thickness of the layer 26 is about 0.5 mm. The implant 22 is positioned as in FIG. 13 with the solid layer 24 uppermost. The upper smooth solid surface of layer 24 allows normal movement of the orbital contents. The implant 22 has incorporated therewith a wetting agent as hereinbefore mentioned. The aforementioned interconnected voids of layer 26 takes on blood throughout the voids in the same manner as hereinbefore described and is biodegraded at a greater rate than the surface 24 due to its greater exposed surface area thereby allowing the layer 24 to remain longer for supporting the orbital contents.

The implant 22 is metabolized as described hereinbefore relative to the bone void dressing member of FIGS. 1-7. A further one piece orbital implant 28 is provided, FIGS. 11 and 12, which is formed of the upper smooth continuous layer 30 of polylactic acid of about 0.5 mm in thickness, with the integral second or lower layer 32 in spun filament form of about 0.5 mm in thickness also of polylactic acid. The spun filament layer 32 has randomly positioned, randomly sized and shaped interconnected voids, each connected with the others and communicating with the outer surface of the layer 32 substantially as shown in FIG. 14. Each of the implants 22 and 28 has incorporated therewith a wetting agent hereinbefore mentioned and applied as illustrated in FIG. 13 and heretofore described.

Occasionally those people afflicted with one of the coagulation defects (such as hemophelia or Von Willenbrand's disease) require extraction of teeth or some other minor surgical procedure. The polylactic acid members described above could be treated as described here to function as a more effective hemostatic agent that is currently available.

The polylactic acid body member, in the interconnected cell form is formed by either the high vacuum foaming process or spun filament process. However, when the polylactic acid is produced or just before the polymer is converted to its final form a therapeutic agent such as a hemostatic agent, thrombin or thromboplastin is mixed into the polylactic acid material liquid. The final product emerges with the hemostatic agent incorporated within the product structure and upon the surfaces of the structional filaments forming the voids of the body member and not in the voids. This method of incorporating the therapeutic agent into the structures material allows the voids formed by the therapeutically treated structural filaments to function as hereinbefore described.

The polylactic framework which is impregnated with hemostatic agent assists the coagulation mechanism in two ways: (1) it functions as a mechanical matrix for the coagulation process as well as reducing the volume of blood needed to occlude the surgical void, (2) the hemostatic agent (thrombin or thromboplastin) chemically interacts with the patient's own functional coagulation factors in such a way as to reduce the effect of the patient's coagulation factor deficit.

Having thus described the invention, what is claimed as new and desired to be secured by Letters Patent is:

1. The method of treating and healing a newly created bone void consisting in forming a one piece body of moldable biodegradable material having enclosed interconnected randomly positioned, randomly sized and randomly shaped voids therein and throughout, each void communicating with the others and communicating with substantially the entire exterior of the body and through which blood is attracted by capillary action to saturate the body with blood for blood vessel development throughout the body and the body of a size adapted to substantially fill the void said voids occupying about 90% of the volume of the body and said body having a wetting agent incorporated therewith, filling the void with the body, then allowing the blood saturated body to remain in the void whereby blood vessels are produced throughout the body and the bone void is healed as the body is biodegraded.

2. The method of claim 1 in which the biodegradable material is polylactic acid polymer.

3. The method of treating and healing tissue deficiencies consisting in forming a body member of a biodegradable material having enclosed interconnected randomly positioned, sized and shaped voids communicating substantially with each other and substantially with the entire exterior of the body, said voids occupying about 90% of the volume of the body and said body having a wetting agent incorporated therewith, then applying the body member to the tissue deficiency, then allowing the body member to remain whereby the tissue deficiency is healed and the body member biodegraded.

4. A device for treating and healing a newly created bone void comprising:
(a) a one piece body member formed of a biodegradable material,
(b) said body member having a form sufficient to fill and cover a bone void, and
(c) having enclosed interconnected randomly positioned and randomly sized and shaped voids therein each void connecting with the others and communicating with the exterior of the body through which voids blood is attracted by capillary action for saturation of the body with blood said voids occupying about 90% of the volume of the body and said body having a wetting agent incorporated therewith, whereby a bone void filled and covered by the body member is healed as the body member biodegrades.

5. The device of claim 4 in which the biodegradable material is polylactic acid polymer.

6. The device of claim 4 in which said body member material has a therapeutic agent incorporated in said material to assist healing.

7. The method of treating and healing a tissue deficiency in the orbital floor consisting in forming a sheet member of a biodegradable material including a first layer having a solid smooth outer surface which is integral with a second opposed layer having enclosed randomly positioned and randomly sized and shaped interconnected voids therein and communicating with the exterior thereof through which blood is attracted by capillary action to saturate the second opposed layer with blood, said voids occupying about 90% of the second layer and said sheet member having a wetting agent incorporated therewith, then applying the sheet member to the tissue deficiency, then allowing the sheet member to remain whereby the tissue deficiency is healed and the sheet member biodegraded.

8. A device for treating a bone fracture comprising:
(a) a one piece body member formed of a biodegradable material,
(b) a first portion of said body member being solid in formation and surrounding in one plane (c) a further portion of said body member having enclosed interconnected randomly sized, randomly poritioned and randomly shaped voids therein; each void connecting with the others and communicating with the exterior of the body through which voids blood is attracted by capillary action for saturation of the body with blood, said voids occupying about 90% of the volume of the further portion and said body member having a wetting agent incorporated therewith, said further body portion biodegrading first and followed by the biodegrading of the first portion. a product being pierced; and means for locking said stripper carriage in position with said stripper plate resting upon a product while said knives are being withdrawn from the product.

* * * * *